Sept. 18, 1973
S. MERHOLZ
Plant Pat. 3,403
BEGONIA PLANT
Filed April 12, 1972
2 Sheets-Sheet 1
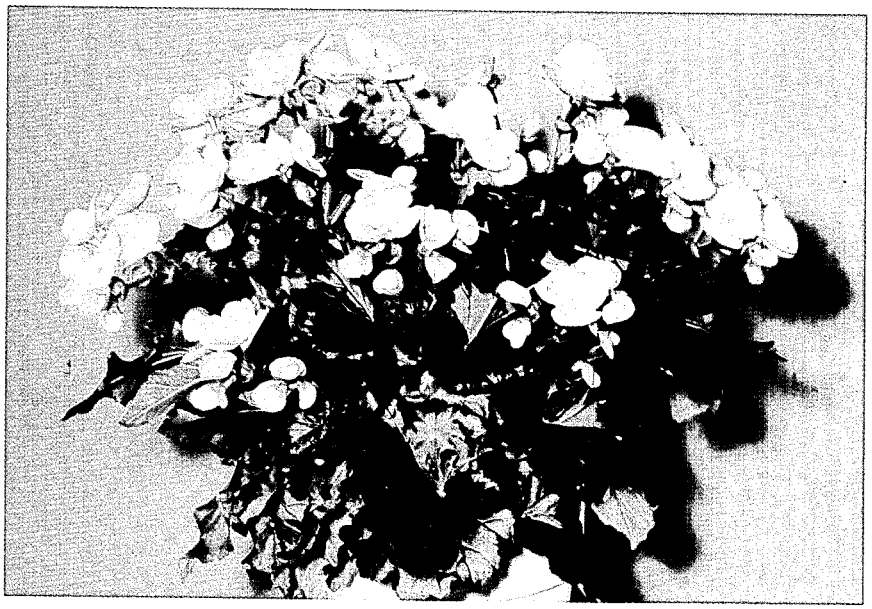

BEGONIA PLANT
Filed April 12, 1972
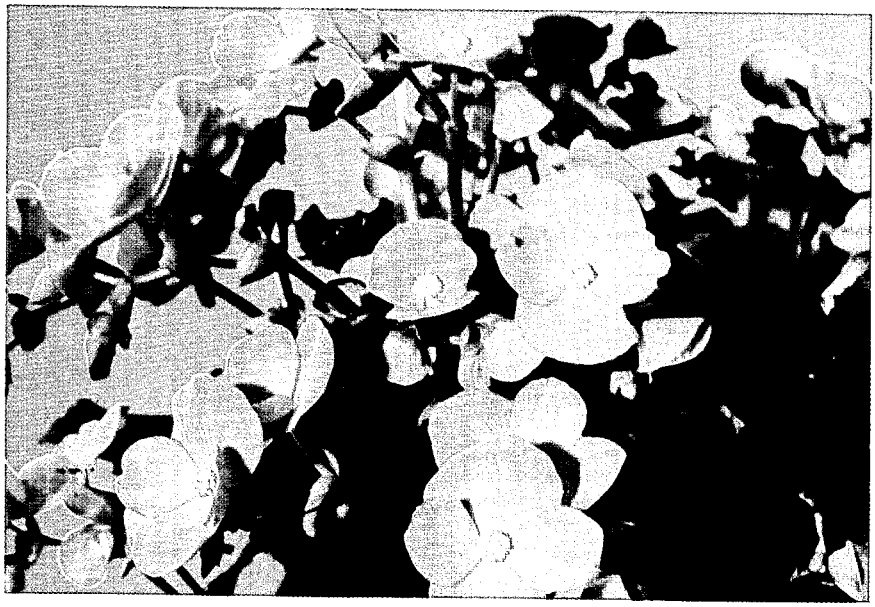

United States Patent Office

Plant Pat. 3,403
Patented Sept. 18, 1973

3,403
BEGONIA PLANT

Siegfried Merholz, Krefeld, Germany, assignor to Mikkelsens Inc., Ashtabula, Ohio Filed Apr. 12, 1972, Ser. No. 243,485
Int. Cl. A01h 5/00
U.S. Cl. Plt.—68 1 Claim The present invention relates to a new and distinctive variety of begonia plant botanically known as *Begonia elatior* discovered by me as a mutation of the commercially known variety Schwabenland, disclosed and claimed in pending U.S. application Ser. No. 158,640, filed June 30, 1971, in the name of Otto Rieger, deceased, by Gertrude Rieger, legal representative.

The new mutation was discovered under cultivation in my nurseries at Krefeld, West Germany, and when asexually reproduced has been found to retain its unique characteristics through successive propagations. Further development and asexual reproduction on a trial basis in Ashtabula, Ohio, has confirmed that the new variety asexually propagates true in other geographical areas.

The most distinguishing characteristics of the new variety when compared with the parent variety are the very red pigmentation in the foliage, the leaf petiole, and the stems, compared to green counterparts of the parent variety, and the bright orange red color of the flowers.

The following, more specific features distinguish the new variety from both its parent and other commercial begonia varieties of this general type presently known and available in the floriculture industry:

(1) Plants are more vigorous but maintain the short compact growth habit of the parent.

(2) Internodal spacing is close.

(3) Foliage is above average in size, heart shaped, indented highly glossy, durable, and mildew resistant.

(4) Leaves, leaf petiole, and main stems are highly colored with red pigmentation.

(5) Older leaves develop a very dark appearance because of the additional pigmentation, thereby offering a new contrast of the flowers.

(6) A deep bright orange red flower color which is more intense than the previously introduced, unpatented cultivar Schwabenland Orange.

(7) The new variety is very floriferous, capable of commercial utilization on a year around basis.

(8) An increase in flower size coupled with improved qualities of texture and durability.

(9) Vegetative reproduction is readily accomplished through propagation of cuttings that root quickly and abundantly, eventually developing basal adventitous shoots allowing for the development of a full plant easily controlled for commercial forcing.

The new variety is illustrated in the accompanying colored photographic drawings, with sheet 1 comprising a typically grown, full plant; and sheet 2 comprising a close up view of a flower cluster. The typical foliage patterns in various stages of development from young to mature leaves can be seen in the photographs.

The following detailed description of the new variety is based on several seasonal observations and critical analysis of a considerable number of plants grown under commercial practices in Krefeld, West Germany. As is the case with nearly all plant materials, natural light, temperatures, and other environmental factors may alter the rate of growth; the pattern and size of the foliage; the size, texture, shape, and color intensity of the flowers. The descriptions herein are based on normal glasshouse practices followed in Germany unless otherwise noted. Color references are to the Royal Horticultural Society Colour Chart, except where general color terms of ordinary dictionary significance are used.

Parentage: Mutation of the variety Schwabenland, which was a hybrid resulting from crossing a mutant of *Begonia bertini compacta* as the seed parent with *Begonia socotrana* as the pollen parent.

Propagation: By asexually propagating many thousands of leaf cuttings, then growing those plants that formed adventitous bud shoots from the base of the leaf petiole and subsequently flowering those plants, it has been demonstrated repeatedly that the mutation is stable and produces true to type.

Rooting habit: Rapid and voluminous production of roots is above average for a begonia of this type. The initiation of adventitous buds on the base of the petiole that develop into vegetative shoots in a short period of time after root initiation is excellent.

Form: Plants tend to be compact with some self-branching giving a semi-dwarf appearance.

Habit of growth: The mutation is very vigorous with strong upright stems having close internodes. The increased vigor is very pronounced in comparison to an earlier mutation commercially known as Schwabenland Orange. This increased vigor allows for a better quality plant during the dull periods of the winter.

Blooming habits: Flowers are usually single with four bracts; occasionally with eight. Blooms flower one at a time carried on trusses. Blooms will usually endure for several weeks. The number of actual blooms vary with the age of the plant and the time of year. When the flowering response has been properly initiated, a general profusion of blooms occurs.

Blooming season: In Germany, the natural flowering season of this mutation is the same as for the parent Schwabenland, namely, late November through early December. When proper regulation of the photo period is applied in conjunction with proper temperature manipulations, the new begonia variety can be brought into flower at any season of the year, making it of further economic value. The intense orange red color of the flowers is acceptable for all seasons. The color contrast of the foliage gives this variety another interesting and useful quality especially for the autumn, winter, and spring seasons.

Foliage: The foliage of the new variety has the same general features of the parent Schwabenland variety, differing therefrom in color, and to some degree, size. The foliage is alternate; borne at a sharp angle to the stem; average to above average in quantity with the following detailed descriptions:

Size.—Foliage would be classified as being rather large for this type of begonia. Environmental conditions can greatly alter the size, texture, and color tones of the foliage.

Shape.—The photographic drawings clearly show the overall oval pointed type leaf with strong indentations similar to a maple leaf. A heart shape is apparent with the setback of the leaf petiole.

Texture.—The upper surface of the leaf is leathery in texture but has a luminescence or sparkle when the plant is grown with good cultural practices. The undersurface of the leaf is glossy as if coated with a film of oil, giving a highly reflective appearance.

Margin.—As illustrated, the young foliage especially is quite indented and notched along the edges. As the foliage matures the edges becomes less indented; the overall leaf flattens and cups slightly downward in an umbrella effect.

Color.—New foliage has a distinctive red tone that is completely different both from the original Schwabenland variety and the unpatented orange mutation known commercially as Schwabenland Orange.

New foliage.—Upper side is green, heavily overlaid with deep red. Under side is dull red toward a shade of red 46–A to 59–B.

Mature foliage.—Upperside is green varying from 139–A and 135–A, with a light overlay of red giving a very dark leaf appearance. The underside of the leaves are yellowish green 147–B, with distinct red pigmentation.

Stems-petioles: The leaf petioles have a strong red coloring approaching a red purple 59–A. The stems when immature also have this type of coloration but become a brownish red to a dark green as they mature.

Disease resistance: The foliage is quite resistant to common mildew infections when compared with other begonia cultivars commonly used in the floricultural industry.

Flowers: Borne on pyramidal trusses with several clusters of three to a stem. Individual flower stems are short to medium in length with sufficient vigor to be upright and self-supporting. Bracts are relatively flat, usually four in number which will give an individual bloom a measurement up to 6 cm. or more in diameter. The vigor of the plant is also expressed in the blooms which have a stronger texture, larger size, and a better overall quality than the blooms of the parent variety. The flowers are nearly exclusively male with a distinctive yellow eye made up of a cluster of stamens and anthers.

Quantity: Very floriferous with flower development over a considerable length of time, often three to four months. The plant itself will usually deteriorate before flowering actually ceases.

Buds: Are flatly folded and progressively develop as the main flowering stem continues to grow and initiates new flowering parts. Then flowering bud closely resembles the shape of a lima bean but develops into a uniformly symmetrical flower.

Petals (bracts): The upper side of the petals is a bright orange red, nearly 40–A, with the under side being dull orange red, nearly 34–A.

Reproductive organs: Flowers are very predominately male; female flowers, when they occur, are terminal.

Stamens.—Are quite prominent and with their bright yellow color give a definite contrast to the coloring of the bracts. The color of the stamens is 14–A.

Pollen.—Is plentiful and lighter yellow in color, 13–B.

Styles/ovaries.—As in most begonias the pistils are divided into three segments or seed capsules.

I claim:

1. A novel and distinctive *elatior Begonia* variety characterized particularly by its increased vigor but short compact growth, with close internodes; the high degree of red pigmentation in the stems, leaf petioles, and foliage thereby giving an overall reddish cast to the plant, with the additional color penetration of the foliage adding considerable contrast to the bright orange red color of the bracts; its very floriferous habit with excellent quality blooms of larger than average size when compared to the parent variety; its high quantity of excellent foliage possessing a high degree of resistance to common mildew; its characteristic of being vegetatively propagated from leaf cuttings that produce vigorously growing adventitious shoots; by its ability to be produced under controlled environmental conditions on a year around basis, and by its excellent keeping qualities under normal household conditions.

No references cited.

ROBERT E. BAGWILL, Primary Examiner